United States Patent [19]

Schraga

[11] Patent Number: 5,643,306

[45] Date of Patent: Jul. 1, 1997

[54] DISPOSABLE LANCET

[75] Inventor: Steven Schraga, Surfside, Fla.

[73] Assignee: Stat Medical Devices Inc., North Miami, Fla.

[21] Appl. No.: 620,565

[22] Filed: Mar. 22, 1996

[51] Int. Cl.$^6$ .................................................. A61B 17/32
[52] U.S. Cl. ........................................ 606/182; 128/770
[58] Field of Search ........................... 606/181–185; 128/770

[56] References Cited

U.S. PATENT DOCUMENTS

| | | | |
|---|---|---|---|
| 4,414,975 | 11/1983 | Ryder et al. | 606/182 |
| 4,449,529 | 5/1984 | Burns et al. | |
| 4,628,929 | 12/1986 | Intengan et al. | |
| 4,794,926 | 1/1989 | Munsch | |
| 4,869,249 | 9/1989 | Crossman et al. | |
| 4,889,117 | 12/1989 | Stevens | |
| 4,892,097 | 1/1990 | Ranalletta et al. | |
| 5,054,499 | 10/1991 | Swierczek | |
| 5,133,730 | 7/1992 | Bro et al. | 606/182 |
| 5,212,879 | 5/1993 | Biro et al. | |
| 5,269,800 | 12/1993 | Davis, Jr. | |
| 5,318,581 | 6/1994 | Sunmo | |
| 5,356,420 | 10/1994 | Czernecki et al. | |
| 5,366,470 | 11/1994 | Ramel | |
| 5,395,388 | 3/1995 | Shraga | 606/181 |
| 5,402,798 | 4/1995 | Swierczek et al. | |
| 5,439,473 | 8/1995 | Jorgensen | |
| 5,454,828 | 10/1995 | Schraga | |

*Primary Examiner*—Michael Buiz
*Assistant Examiner*—William W. Lewis
*Attorney, Agent, or Firm*—Greenblum & Bernstein P.L.C.

[57] ABSTRACT

Single use disposable lancet devices are disclosed as inexpensive, easy to use, and safe instruments for the piercing or cutting of a patient's skin to obtain small amounts of blood for diagnostic purposes. The devices described readily visually indicate, upon casual observance, whether or not they have yet been used. A locking device is further provided to physically prevent re-use of the devices after they have been used once.

21 Claims, 6 Drawing Sheets

DISPOSABLE LANCET

BACKGROUND OF THE INVENTION

1. Field of the Invention

The invention concerns a lancet device which is suitable for a single use only and which is effectively unusable after a single use. The device also includes indicators by which a user can readily visibly determine whether or not the device has been used yet.

2. Description of Background information

Sharp pointed or bladed lancets are frequently used to make a small penetration of a patient's skin to let a small volume of blood for diagnostic purposes. With the growing concern over blood-transmitted communicable diseases such as AIDS, hepatitis, etc., it is becoming increasingly critical to insure that a needle or lancet, once used, is not re-used on a different patient. Thus, precautions are necessary to insure that once used, a lancet cannot be accidentally used again. Furthermore, because of the continuing threat that a used lancet poses even after disposal, it is paramount that the lancet tip be completely and securely shielded after use and disposal, to prevent accidental contact with sanitation workers or anyone else that might accidentally come into contact with the device.

Spring-energized, i.e., preloaded spring driven lancets of many types have been known and used as a replacement for needles for piercing the skin for blood samples. Some of these devices are designed as single use, disposable devices. However, the relative complexity of such devices has made them expensive to manufacture and, often, unreliable in use. For example, the preloaded spring can often lead to misfiring of the lancet tip or skewing of the spring so as to make an unacceptable incision or an incision which imparts more pain to the patient than absolutely necessary.

U.S. Pat. No. 5,356,420 discloses a preloaded device in which a puncturing tip 7 is mounted on a piston 5 within a piston sleeve 1. A power spring 9 is preloaded within the sleeve and actuated by depression of a push-button 2. An additional spring 10 is provided to ensure that the puncturing tip 7 is retracted into the sleeve after use.

Simpler disposable lancet devices which do not employ preloaded spring driving have also been devised. For example, U.S. Pat. No. 4,889,117 discloses a disposable lancet (FIGS. 7 and 8) in which a needle tip 48' is provided within a tube 50. A cap 44 is provided at one end to the tube 50. Upon depression of the cap 44, the tip 48' protrudes from the tube 50 and pierces the skin of the patient. A spring steel formed washer 60 is provided to ensure that the tip is retracted back within the tube 50 when the force is removed from the cap 44. An inwardly biased tang 62 prevents re-use of the lancet after the initial use. However, with this type of device, where a driving force implied to the cap is in the direction of the patient's skin, when the operator operates the device, the force applied for operation may apply an excessive force to the skin, which may result in unnecessary tissue damage.

U.S. Pat. Nos. 5,133,730 and 5,212,879 disclose a disposable, retractable finger stick device and method for manufacturing the same. Within a housing 12, a blade 14 is provided. A lever arm 16 protrudes from the housing 12. Upon depression of the lever arm 16, the lever arm moves a biasing member 60 to press a ramp 52 to depress a blade holder 50, thereby causing the blade 14 to protrude beyond the housing 12 and pierce the skin of the patient. The biasing member 60 locks against the ramp portion of the blade holder 50 after a single use, to thereby prevent re-use of the device. The blade and blade holder are mounted on a living hinge 48 which helps to retract the blade back within the housing after use. This device has a relatively large number of moving parts and a relatively complex arrangement, thereby increasing the cost of production.

With regard to the device disclosed in U.S. Pat. Nos. 5,133,730 and 5,212,879, as well as the device disclosed in U.S. Pat. No. 4,889,117, an operator cannot readily determine, by looking at the device, whether or not it has been used. Thus, even though an operator would not be able to accidentally stick a second patient with one of these lancets after it had already been used, a real risk still exists with the use of these devices. Because the operator cannot visually determine whether or not the lancet has been used. The possibility exists that the operator will assume that a used device has not been used. In this case, the operator will not ultimately be able to actually stick another patient. However, the operator could possible contact a second patient's skin with the housing in the location at which the blade is intended to protrude during sticking. Since in this instance, the lancet would already have been used, there is a good chance that the housing would be contaminated in this location with blood or other infectious contaminants. Thus, a real risk exists that such contaminants could be transferred to the second patient merely by contacting the housing of the used lancet device with the second patient's skin.

Thus, there is need for a simple, inexpensive, reliable, self-activating disposable lancet device which clearly indicates whether or not the device has been used.

SUMMARY OF THE INVENTION

One advantage of the present invention is the provision of a disposable lancet device which is composed of a minimal number of parts which are inexpensive to produce and easy to assemble.

Another advantage of the present invention is the provision of an indicator which assumes two distinct positions, that are clearly recognizable and distinguishable to the casual observer. One position indicates that the lancet device has not yet been used, and the other position indicates that the device has been used and should be disposed of.

It is another object of the present invention to provide an ergonomically comfortable housing for a lancet device, which an operator can easily operate with only one hand, and in which only two fingers are absolutely required for operation.

It is a further object of the present invention to provide a disposable lancet device, in which the sharp tip of the device is exposed from the housing only very momentarily, during the actual sticking process, and at all other times is safely covered by the housing.

Other objects and advantages of the present invention and advantageous features thereof will become apparent as the description proceeds herein.

Included in the description is a single use disposable lancet device comprising a housing and a spring mechanism pivotally mounted to the housing. The spring mechanism includes a sharpened end. The spring mechanism is mounted within the housing in a substantially unbiased state prior to use. An actuator for biasing the spring mechanism is movable, with respect to the housing, from an initial position to a biasing position to a locked position, in that order.

The actuator includes a locking device which engages the spring mechanism for preventing movement of the actuator from the locked position. The housing includes an opening sized to permit the sharpened end to protrude therethrough exteriorly of the housing upon biasing of the spring mechanism, and the sharpened end retracts back inside of the housing when in the locked position.

The spring mechanism is mounted within said housing in a substantially unbiased state when the actuator is in the initial position. The spring mechanism is biased by the actuator when the actuator is in the biased position, causing the sharpened end to protrude from the housing. The spring mechanism returns to a substantially unbiased state when the actuator is in the locked position.

A pivot post is mounted within the housing. The spring mechanism is pivotally mounted around the pivot post and is pivotally biased with respect to the pivot post upon biasing by the actuator. A stop is mounted within the housing. A second end of the spring mechanism, which is the end opposite to the sharpened end, abuts against and is stopped from movement in a predetermined direction by the stop during biasing of the spring mechanism.

The housing includes two face components joined by a peripheral surface to form a compartment within. In a preferred embodiment, the actuator is mounted substantially centrally of one of the face components of the housing. In another preferred embodiment, the actuator is mounted through the peripheral surface of the housing.

Preferably, the housing is substantially disk-shaped with the two face components comprising two substantially circular faces and the peripheral surface joining the circular faces along circumferential edges. However, other shapes may also be employed.

The actuator preferably includes a button actuatable by one or more fingers of a user, a shaft extending from the button and extending into said housing, and a biasing portion for contacting and biasing the spring mechanism upon movement of the actuator from the initial position to the biasing position. The button visibly extends from the housing when in the initial position, so that an operator can easily see that the device has not yet been used.

The biasing portion of the actuator, in one embodiment, includes a ramped fin extending from the shaft for progressive biasing of the spring mechanism as the button is pushed nearer the housing, from initial position through said biasing position. In this embodiment, the locking device includes a notch formed between an end of the ramped fin, the shaft, and the button. Upon fully depressing the button so that it abuts the housing, the spring mechanism slides off the ramped fin and into the notch, thereby returning to a substantially unbiased condition and preventing return of the actuator to the initial position.

Thus, when the actuator is in the initial position, a user can readily visually identify the initial position by the spacing of the button from the housing surface, and know that the lancet device has yet to be used. On the other hand, when the actuator is in the locked position, a user can readily visually identify the locked position by the position of the button abutting against the housing surface, and know that the lancet device has been used and is to be disposed of.

The actuator further includes a flange extending from an end of the shaft opposite an end of the shaft that is connected to and extends from the button. The flange abuts the spring mechanism in the initial position and prevents removal of the actuator from the housing.

In another embodiment, the biasing portion of the actuator includes a taper on an end of the shaft opposite an end of the shaft extending from the button, and an untapered portion of the shaft extending from the taper for progressive biasing of the spring mechanism as the button is pushed nearer the housing, from the initial position through the biasing position. In this embodiment, the locking device includes a notch formed in the shaft, between the untapered portion and the end of said shaft extending from the button. Upon fully depressing the button so as to abut the housing, the spring mechanism slides off the untapered portion of the shaft and the notch, thereby returning to a substantially unbiased condition and preventing return of the actuator to the initial position.

Thus, when in the initial position, a user can readily visually identify the initial position by the spacing between the button and the housing surface, and know that the lancet device has yet to be used. On the other hand, when the actuator is in the locked position, a user can readily visually identify the locked position by the contact between the button and the housing surface, and know that the lancet device has been used and is to be disposed of.

In this embodiment, the actuator further includes a flange extending from the shaft between the notch and the end of the shaft which extends from the button. The flange abuts an internal surface of the housing when the actuator is in the initial position and prevents removal of the actuator from the housing.

In yet another embodiment, the locking device includes a keyway formed through the shaft, between the untapered portion of the shaft and the end of the shaft extending from the button. Upon fully depressing the button so as to abut the housing, the spring mechanism slides off the untapered portion and into the keyway, thereby returning to a substantially unbiased condition and preventing return of the actuator to the initial position.

Thus, when the actuator is in the initial position, a user can readily visually identify the initial position by the spacing between the button and the housing surface, and know that the lancet device has yet to be used. On the other hand, when the actuator is in the locked position, a user can readily visually identify the locked position by the contact between the button and the housing surface, and know that the lancet device has been used and is to be disposed of.

In this embodiment, the actuator further includes a flange extending from the shaft between the keyway and the end of the shaft which extends from the button. The flange abuts an internal surface of the housing when the actuator is in the initial position, thereby preventing removal of the actuator from the housing.

Further disclosed is a single use disposable lancet device including a housing, a spring mechanism mounted to the housing, an actuator for biasing the spring mechanism, means for indicating that the lance device has not been used and means for indicating that the lance device has been used. The spring mechanism has a sharpened end, and is mounted within the housing in a substantially unbiased state.

The actuator is movable, with respect to the housing, to bias the spring mechanism to extend the sharpened end so as to protrude from the housing. The device further includes means for preventing re-use of the lancet device after a single use has been accomplished. The actuator includes a button actuatable by one or more fingers of a user, a shaft extending from the button and extending into the housing and a biasing portion for contacting and biasing the spring mechanism upon movement of the button toward the housing, from the initial position to the biasing position.

Preferably, the means for indicating that the lancet device has not been used includes a position of the button with respect to the housing wherein the button visibly extends from the housing to show that the lancet device has not been used. Preferably, the means for indicating that the lancet device has been used includes a position of the button with respect to the housing wherein the button visibly contacts the housing to show that the lancet device has been used. Preferably, the means for preventing re-use of the lancet device after a single use has been accomplished includes a locking mechanism which locks the button in the position wherein the button contacts the housing, thereby preventing retraction of the button and preventing the actuator from biasing the spring mechanism more than one time.

The button can be constructed and arranged in various manners and can have various shapes. For example, the button can have an enlarged element at its upper portion that contacts or substantially contacts the housing in the locked position. Alternatively, the button can comprise a cylindrical shaft having an upper portion that is substantially flush with the surface of the housing in the locked position. At least the upper portion of the cylindrical shaft can be of a different color than the housing to enable easy visualization of the button in its protruding, unused position, and in its locked, used position.

Still further, the button can include an element thereon that maintains the button in the initial position. For example, there can be a protrusion on the shaft of the button that prevents the button from being pressed into the housing to an extent that would cause the needle to protrude from the housing. Thus, the shaft of the button can include a breakable protrusion thereon that would require its removal prior to use of the device. Alternatively, a hole can be included in the shaft through which a removable C-clip or a removable tubular member could be inserted to prevent premature activation of the device.

BRIEF DESCRIPTION OF THE DRAWINGS

The present invention is further explained in the description which follows with reference to the drawings, illustrating, by way of non-limiting examples, various embodiments of the invention, with like reference numerals representing similar parts throughout the several views, and wherein.

DESCRIPTION OF THE PREFERRED EMBODIMENTS

Figure 1:
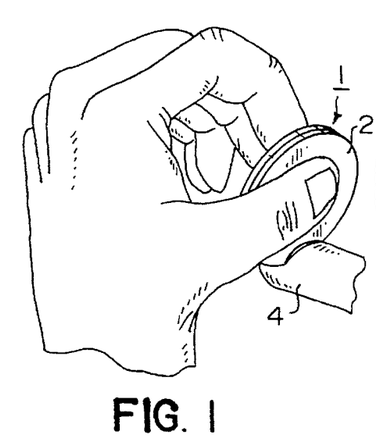
FIG. 1 is a perspective view showing the use of a first embodiment of the present invention in a sticking operation of a patient's finger.

Referring now to the drawings in detail, FIG. 1 shows one embodiment of the present invention in use. The device 1 includes a substantially disk shaped housing 2 which is designed to be relatively small, lightweight and easy to manipulate, such that the operator can operate the device using only one hand. The housing 2 is preferably formed of molded plastic, but may also be made of light metals, composites or other well-known materials. Thus, an operator can take a blood sample from himself or herself without any assistance necessary from another person. Additionally, in the clinical setting, an operator can take a blood sample, e.g., lance a patient's skin, using only one hand, while simultaneously performing another function with the other hand. For example, the operator could steady the patient's arm with the hand that is not used to operate the lancet.

Figure 2:
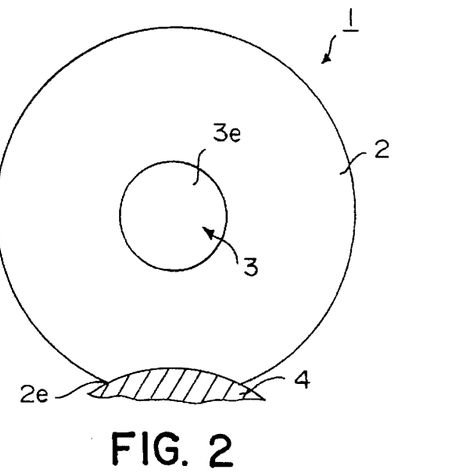
FIG. 2 is a plan view of the first embodiment, shown contacting a cross-section of a patient's finger.
Figure 3:
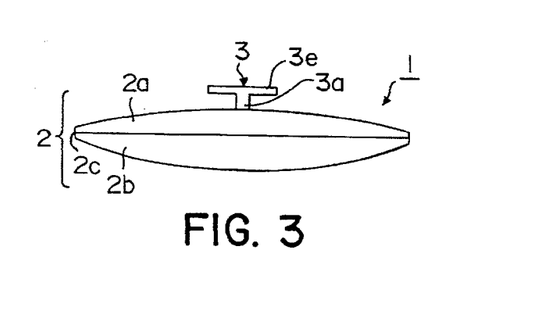
FIG. 3 is a side view of the first embodiment showing the actuator in an initial position.

Protruding from the housing 2 is an actuator 3 (see FIGS. 2 and 3), including a button 3e which the operator depresses in order to operate the lancet, i.e., to control the lancet to perform the lancing function of the patient's skin. In the embodiment shown in FIGS. 1–4, the lancet is ergonomically designed to have a substantially disk-shaped housing, with two substantially circular shaped faces 2a and 2b that taper to join together circumferentially with a peripheral surface 2c to form a hollow compartment within. The faces 2a, 2b and peripheral surface 2c form a substantially concave contour 2e in the area of the device through which a sharpened tip is designed to protrude to perform the lancing function. The concave contour 2e includes an opening 2f through which the sharpened tip passes. The substantially concave contour 2e facilitates the alignment of the lancet device with the patient's skin, for lancing an earlobe, arm, toe, finger, etc., and is particularly well-suited for alignment with a patient's finger. The actuator 3 extends substantially perpendicularly from substantially the center of face 2a as shown in FIGS. 2 and 3. The body and button are designed so that the lancet can easily be grasped and held between the thumb and one or more fingers of a single hand. The button is easily depressed by a thumb or one or more fingers to cause extension of a cutting or piercing instrument from the body 2.

Figure 5:
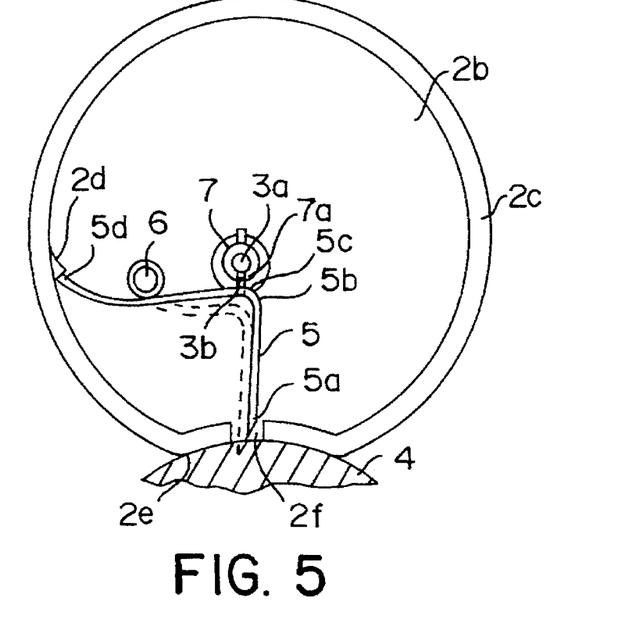
FIG. 5 is a sectional view taken midway around the perimeter of the device according to the first embodiment.

FIG. 5 shows a sectional view of the device shown in FIG. 2, taken midway between the faces 2a and 2b, i.e., with the face 2a and button 3a not shown. Although face 2a is not shown, both faces 2a and 2b are circumferentially reinforced where they meet to form the peripheral surface 2c. A spring mechanism 5 is provided within the compartment formed by the housing 2. The spring mechanism 5 is pivotally mounted to the inside surface of face 2b and pivots about pivot post 6. Pivot post 6 may be a shaft which is mounted to face 2b or may be integrally formed, preferably as one piece with the face 2b. Also, pivot point 6 can be associated with face 2a.

In a preferred embodiment, the spring mechanism 5 is formed of spring steel and may be flat or round in cross-section. However, it is envisioned that the spring mechanism could be formed from plastic, composites or other metals. A first end 5a of the spring mechanism is sharpened into the form of a point or blade to perform the piercing or cutting operation of the skin. Preferably, the sharpened point or blade 5a is integrally formed with the spring mechanism. Alternatively, however, a needle tip or lancet blade could be fixed to the first end of the spring mechanism.

The spring mechanism bends at a distinct angle 5b to form an actuation surface against which the actuator 3 biases the spring mechanism 5. The spring mechanism preferably raps around pivot 6 which fixes the spring around a point about which to pivot when actuated. Alternatively, the spring mechanism could be fixed at a pivot point without actually wrapping around a shaft. A second end 5d of the spring mechanism abuts against a protrusion 2d which is formed in the housing such as on one or both faces 2a and 2b. The protrusion 2d acts as a stop to stop the second end 5d of the spring from moving in an upward direction, and prevents the spring from its tendency to move upward as a reaction to the downward biasing of the first end 5a by the actuator 3 via the actuation surface 5c. Accordingly, by stopping the second end as noted, potential energy is stored within the spring mechanism 5 upon downward actuation of the sharpened end.

Figure 6:
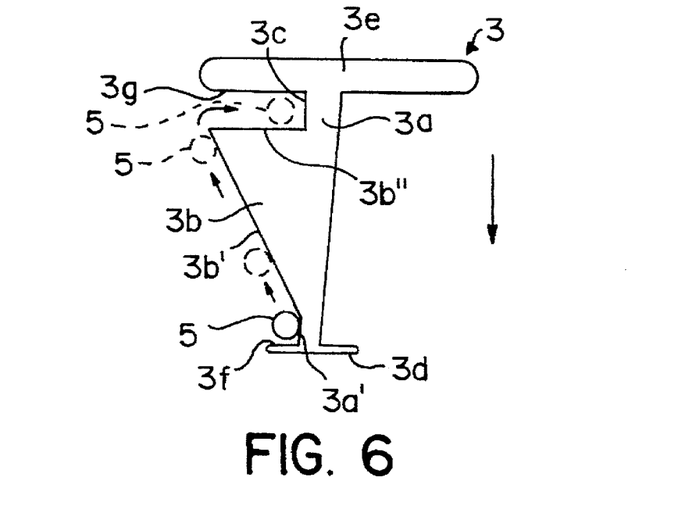
FIG. 6 is a side view of the actuator according to the first embodiment.

A cross-section of shaft 3a of actuator 3 appears substantially in a central location of face 2b in FIG. 5. A biasing portion 3b is shown extending from the shaft 3a. FIG. 6 shows a side view of the entire actuator 3. Button 3e is fixed substantially perpendicularly at one end of shaft 3a. In this embodiment, the biasing portion 3b is a ramped fin which extends radially from the shaft 3a. The fin 3b begins as a very narrow portion near the lower end of shaft 3a, and constantly widens in a direction toward the upper end of shaft 3b to form a ramped edge 3b'. A portion of the shaft 3a' extends below the ramped fin 3b to form an initial, substantially unbiased position for the spring 5 when the actuator 3 is in the initial position, i.e., when actuator 3 is in the position shown in FIG. 3, and no biasing force is applied against the spring 5.

At the lower end of the shaft 3a, a flange 3d is fixed and extends substantially perpendicularly therefrom. The upper surface 3f of flange 3d abuts against the spring 5 in the initial position and prevents removal of the actuator 3 from the housing 2. A guide 7 is mounted to the interior of face 2b, and includes a slot 7a through which the ramped fin 3b passes. The guide 7 ensures that the actuator 3 cannot rotate so that the fin 3b always remains aligned with the actuation surface 5c of the spring 5. The guide 7 also acts as additional insurance that the actuator cannot be removed from the housing, since flange 3d would abut against the guide 7, thereby preventing removal of the actuator, even if for some reason the spring 5 would fail to prevent the removal.

A side view of the lancet device, in the initial position, is shown in FIG. 3. In the initial position, the spring 5 abuts against the lower end 3a' of the shaft 3a as noted above. In this position, the button 3e and upper end of the shaft 3a extend from the face 2a of the housing 2 as shown in FIG. 3. The extension of the button 3e so as to separate it from face 2a is distinctly visible to even a casual observer. Thus, an operator can readily visibly identify a lancet device which has not been used.

The lancet according to the present embodiment operates as follows: The operator grasps the single use disposable lancet device 1 between a thumb and one or more fingers of a single hand. The operator then contacts the skin of a patient to be lanced with the substantially concave contour 2e of the device as shown in FIGS. 1 and 2. To perform the lancing function, the operator depresses button 3e until the button makes contact with the face 2a. The operator then removes the lancet device from contact with the patient's skin and disposes of the lancet device, after which the patient's blood sample may be taken and analyzed.

Referring again to FIGS. 5 and 6, a description of the functions of the actuator 3 and spring mechanism 5 will now be described. As the operator depresses the button 3e, the entire actuator mechanism 3 moves in a downward direction (the direction of the arrow shown in FIG. 6) with respect to the housing 2 and spring mechanism 5. Because of this relative movement, the spring mechanism is forced to move along the actuating position of the ramped surface 3b' of the biasing portion 3b, as shown in phantom positions in FIG. 6. This relative movement along the ramped portion causes the biasing mechanism to exert a biasing force against the spring mechanism, which translates to a forced movement of the spring mechanism in a downward direction. At the maximum width of the biasing ramp 3b, the sharpened end 5a protrudes to its maximum position beyond the housing 2 as shown in phantom lines in FIG. 5, thereby piercing the skin of the patient.

As the operator continues to push the actuator into the housing (i.e., in the "downward" direction described above), the spring slips off the ramped edge 3b' and into notch 3c, into the locking position, where the spring mechanism again abuts the shaft 3a. This results in a rapid return of the spring mechanism and the sharpened end 5a back into the housing 2 as shown in the solid lines in FIG. 5. The driving force of the return of the sharpened point 5a into the housing, is the potential energy which has been stored in the spring mechanism 5, which is converted to kinetic energy when the spring mechanism 5 is no longer biased by the ramped edge 3b'.

The notch 3c is formed by an upper surface of the biasing portion meeting with the shaft 3a, which in turn meets with a bottom surface 3g of the button 3e, as shown in FIG. 6. When the spring mechanism rests in the locking position, in a substantially unbiased condition, in notch 3c, the actuator 3 is effectively prevented from being withdrawn or slid back out of the housing to again assume the initial position. That is, the spring mechanism 5 abuts the upper surface of the biasing portion, as shown in phantom lines in FIG. 6, when the spring mechanism and actuator are in the locked position. Thus, even if a person tries to physically retract the button 3e away from the housing 2, the person is prevented from doing so because the spring mechanism 5 prevents the upward movement of the actuator with respect to the housing.

Figure 3A:
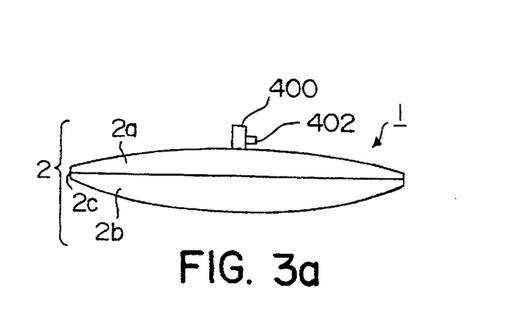
FIGS. 3a and 3b illustrate an alternative construction of the button.
Figures 3B, 4:
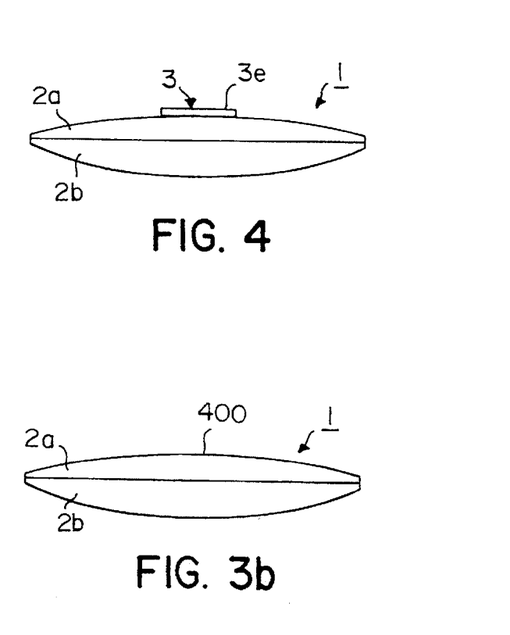
FIG. 4 is a side view of the first embodiment showing the actuator in a used and locked position.

A side view of the lancet device, in the locked position, is shown in FIG. 4. As described above, in the locked position, the spring 5 abuts against the upper surface 3b" of the biasing portion 3b and against the shaft 3a. In this position, the button 3e contacts the outer surface of the face 2a as shown in FIG. 4. This contact of the button 3e with the surface of the face 2a is distinctly visible to even a casual observer. Thus, an operator can readily visibly identify a lancet device which has been used and needs to be discarded. This readily identifiable feature of the device prevents even a second contact of the device with the skin of a second patient, while also positively preventing a re-use of the device.

As discussed above, the button can be constructed and arranged in various manners and can have various shapes other than specifically illustrated in the drawings. For example, the button can have an enlarged element at its upper portion that contacts or substantially contacts the housing in the locked position, as illustrated. Alternatively, as illustrated in FIGS. 3a and 3b, the button can comprise a cylindrical shaft 400 having an upper portion that is substantially flush with the surface of the housing in the locked position. At least the upper portion of the cylindrical shaft can be of a different color than the housing to enable easy visualization of the button in its protruding, unused position, and in its locked, used position.

Still further, the button, in any of the embodiments, can include an element thereon that maintains the button in the initial position. For example, there can be a protrusion 402 on the shaft of the button that prevents the button from being pressed into the housing to an extent that would cause the needle to protrude from the housing. Thus, the shaft of the button can include a breakable protrusion thereon that would require its removal prior to use of the device. Also, a hole can be included in the shaft through which a removable C-clip or a removable tubular member could be inserted to prevent premature activation of the device.

Figure 7A:
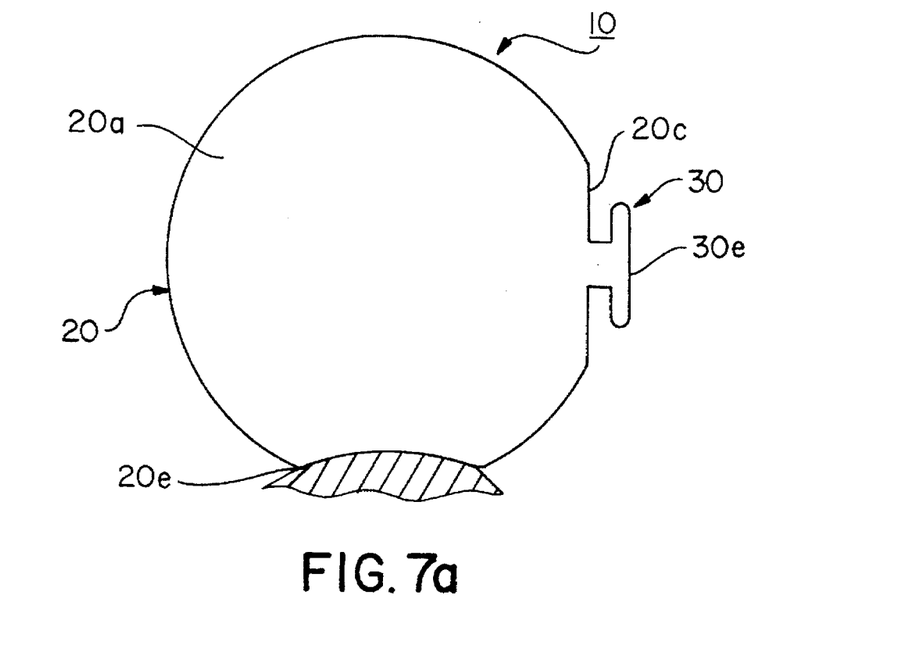
FIG. 7a is a perspective view of a second embodiment according to the present invention.
Figure 7B:
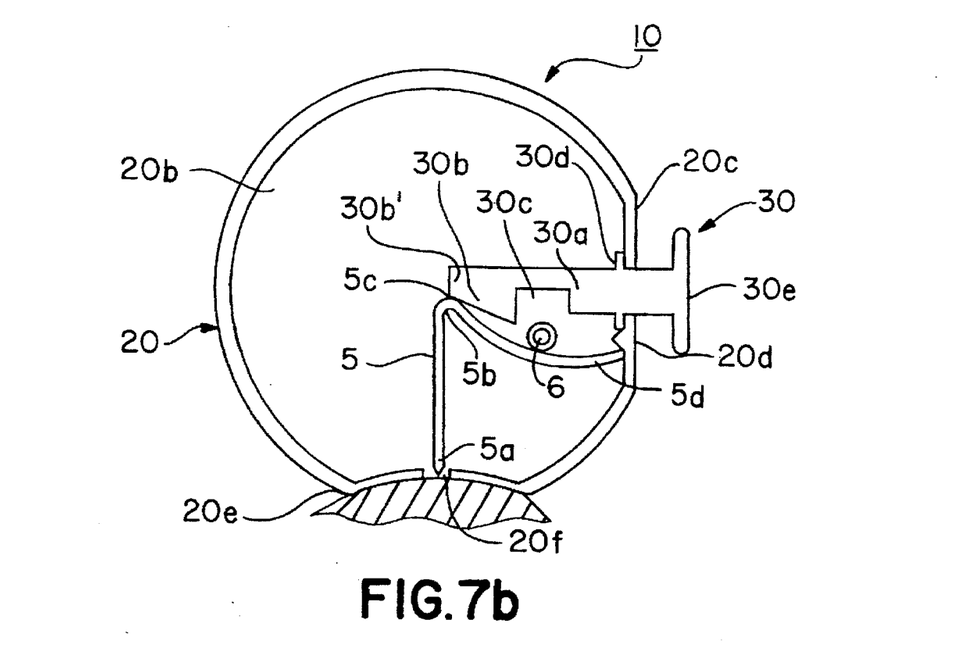
FIG. 7b is a sectional view of the second embodiment, with one face of the housing removed, showing the actuator in an initial position.
Figure 8:
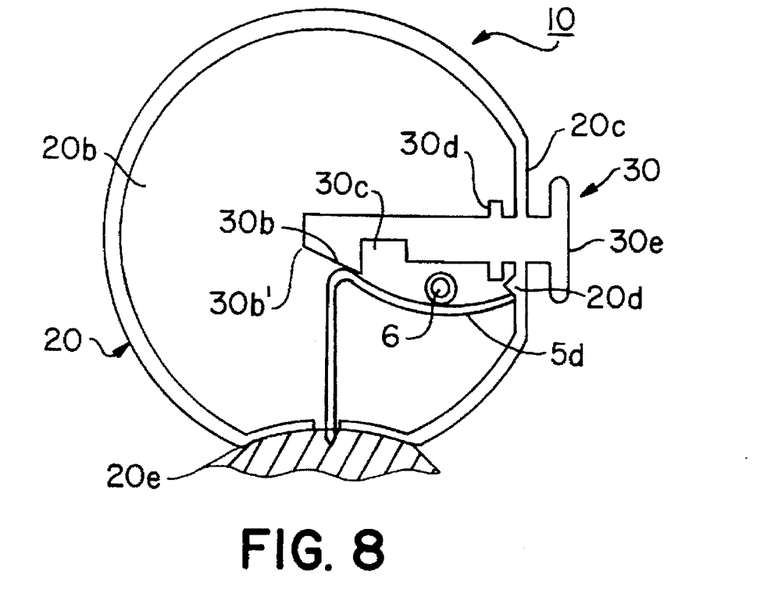
FIG. 8 is a sectional view of the second embodiment, with one face of the housing removed, showing the actuator in a biasing position.
Figure 9:
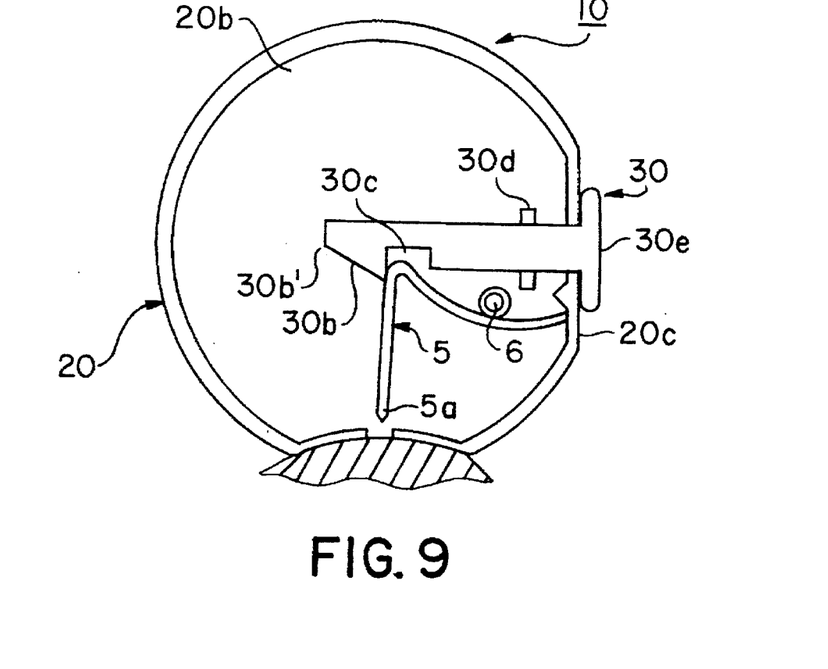
FIG. 9 is a sectional view of the second embodiment, with one face of the housing removed, showing the actuator in a used and locked position.

FIGS. 7–9 show another embodiment of a single use disposable lancet device according to the present invention. In this embodiment, the actuator 30 of the device 10 protrudes through a position on the peripheral surface 20c of the housing 20. Each of FIGS. 7b–9 shows a view of the second embodiments of the device having the face 20a removed. FIG. 7a shows the second embodiment with the face 20a in place. Both faces 20a and 20b are circumferentially reinforced where they meet to form the peripheral surface 20c. A spring mechanism 5 is provided within the compartment formed by the housing 20. The spring mechanism 5 is pivotally mounted to the inside surface of face 20b and pivots about pivot post 6. Pivot post 6 may be a shaft which is mounted to face 20b or may be integrally formed with the face 20b.

In this embodiment, the spring mechanism 5 is formed of spring steel and may be flat or round in cross-section. However, it is envisioned that the spring mechanism could be formed from plastic, composites or other metals. A first end 5a of the spring mechanism is sharpened into the form of a point or blade to perform the piercing or cutting operation of the skin. Preferably, the sharpened point or blade is integrally formed with the spring mechanism. Alternatively, however, a needle tip or lancet blade could be fixed to the first end of the spring mechanism.

The spring mechanism bends at a distinct angle 5b to form an actuation surface 5c against which the actuator 30 biases the spring mechanism 5. The spring mechanism preferably raps around pivot 6 which fixes the spring around a point about which to pivot when actuated. Alternatively, the spring mechanism could be fixed at a pivot point without actually wrapping around a shaft. A second end 5d of the spring mechanism abuts against a protrusion 20d which is formed in the housing. The protrusion 20d acts as a stop to stop the second end of the spring from moving in an upward direction, and prevents the spring from its tendency to move upward as a reaction to the downward biasing of the first end 5a by the actuator 30 via the actuation surface 5c. Accordingly, by stopping the second end as noted, potential energy is stored within the spring mechanism 5 upon downward actuation of the sharpened end.

As shown in FIGS. 7–9, a portion of the peripheral surface 20c of the housing 20 is substantially flattened in the areas through which the actuator 30 protrudes. The actuator 30 includes an actuation button 30e which is fixed substantially perpendicularly at one end of shaft 30a. A biasing portion 30b of the shaft 30a includes a tapered end 30b' for smooth engagement of the actuation surface 5c when the actuator is slid inwardly with respect to the housing. The tapered portion 30b' ramps progressively to the outer diameter of the shaft 30a which forms the maximum actuation position of the actuator and spring mechanism, at which position, the sharpened end 5a extends to its maximum position beyond the housing 20. The sharpened end 5a is shown in its maximally extended actuation position in FIG. 8.

As the operator continues to push the actuation button 30e towards the housing surface 20, the biasing portion 30b of the actuator bypasses actuation surface 5c of the spring mechanism 5, at which time the actuation surface 5c slips off the biasing portion 30b and into notch 30c, into the locking position, as shown in FIG. 9. This results in a rapid return of the spring mechanism and the sharpened end 5a back into the housing 20 as also shown in FIG. 9. The driving force of the return of the sharpened point 5a into the housing, is the potential energy which has been stored in the spring mechanism 5, which is converted to kinetic energy when the spring mechanism 5 is no longer biased by the biasing portion 30b.

When the spring mechanism 5 rests in the locking position, in a substantially unbiased condition, in notch 30c, the actuator 30 is effectively prevented from being withdrawn or slid back out of the housing to again assume the initial position. That is, the spring mechanism 5 abuts the surface of the notch 30c when an attempt is made to withdraw the actuator from the housing. Thus, even if a person tries to physically retract the button 30e away from the housing 20, the person is prevented from doing so because the spring mechanism 5 prevents the outward movement of the actuator with respect to the housing.

In this embodiment, the actuator does not contact the spring mechanism in the initial position, so that the spring rests in a substantially unbiased state in the initial position.

The shaft 30a is further provided with a flange 30d fixed and extending substantially perpendicularly therefrom, between the notch 30c and button 30e. Flange 30d abuts against the inner surface of the housing 20 in the initial position and prevents removal of the actuator 30 from the housing 20, as shown in FIG. 7. The compartment formed by faces 20a and 20b are manufactured to a tolerance sufficient to maintain the actuator 30 in alignment with the spring mechanism 5 in this embodiment.

Similar to the first embodiment, when this embodiment is in the initial position, as shown in FIG. 7, the button 30e and an end of the shaft 30a extend from the peripheral surface 20c. This extension of the button 30e from the peripheral surface 20c is distinctly visible to even a casual observer. Thus, an operator can readily visibly identify a lancet device which has not been used.

The lancet according to the present embodiment operates as follows: The operator grasps the single use disposable lancet device 10 between a thumb and one or more fingers of a single hand. The operator then contacts the skin of a patient to be lanced with the substantially concave contour 20e of the device as shown in FIGS. 7a and 7b. To perform the lancing function, the operator depresses button 30e until the button makes contact with the peripheral surface 20c. The operator then removes the lancet device from contact with the patient's skin and disposes of the lancet device, after which the patient's blood sample may be taken and analyzed.

As the operator depresses the button 30e, the entire actuator mechanism 30 moves inwardly with respect to the housing 20 and spring mechanism 5. Because of this relative movement, the spring mechanism is forced to move along the actuating position of the ramped surface 30b' of the biasing portion 30b, and then against the shaft surface actuation portion 30b. This relative movement along the ramped portion and shaft surface causes the biasing mechanism to exert a biasing force against the spring mechanism, which translates to a forced movement of the spring mechanism in a downward direction, thereby driving the sharpened end 5a out of housing 20, through opening 20f and through the skin of the patient as shown in FIG. 8.

As the actuator passes the actuating position and the lancing function is completed, the spring is then returned to the locked position, as described above and as shown in FIG. 9. In this position, the button 30e contacts the outer surface of the peripheral surface 20c. This contact of the button 30e with the peripheral surface 20c is distinctly visible to even a casual observer. Thus, an operator can readily visibly identify a lancet device which has been sued and needs to be discarded. This readily identifiable feature of the device prevents even a second contact of the device with the skin of a second patient, while also positively preventing a re-use of the device.

FIGS. 10–13 show yet another embodiment of a single use disposable lancet device according to the present invention. This embodiment functions substantially similarly to the embodiment shown in FIGS. 7–9, with the only difference being in the configuration of the locking device. As such, only the locking device will be specifically described.

Figure 12:
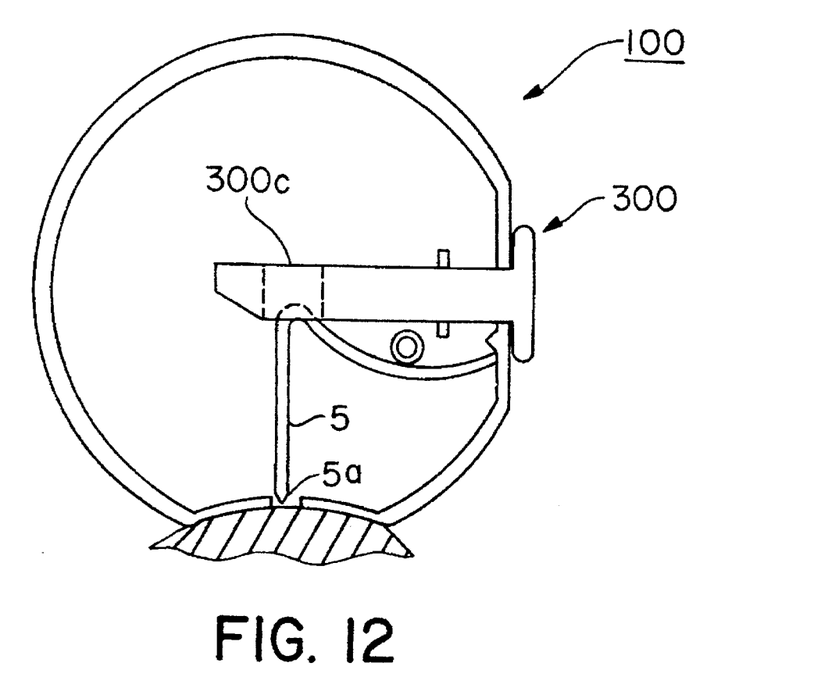
FIG. 12 is a sectional view of the third embodiment, with one face of the housing removed, showing the actuator in a used and locked position.

During actuation of the device, as the operator continues to push the actuation button 300e towards the housing surface 20c, the biasing portion 300b of the actuator bypasses actuation surface 5c of the spring mechanism 5, at which time the actuation surface 5c slips off the biasing portion 300b and into keyway 300c, into the locking position, as shown in FIG. 12. This results in a rapid return of the spring mechanism and the sharpened end 5a back into the housing 20 as also shown in FIG. 12. The driving force of the return of the sharpened point 5a into the housing, is the potential energy which has been stored in the spring mechanism 5, which is converted to kinetic energy when the spring mechanism 5 is no longer biased by the biasing portion 300b.

When the spring mechanism 5 rests in the locking position, in a substantially unbiased condition, in keyway 300c, the actuator 300 is effectively prevented from being withdrawn or slid back out of the housing to again assume the initial position. That is, the spring mechanism 5 abuts the surface of the keyway 300c when an attempt is made to withdraw the actuator from the housing. Thus, even if a person tries to physically retract the button 300e away from the housing 20, the person is prevented from doing so because the spring mechanism 5 prevents the outward movement of the actuator with respect to the housing.

Figure 10:
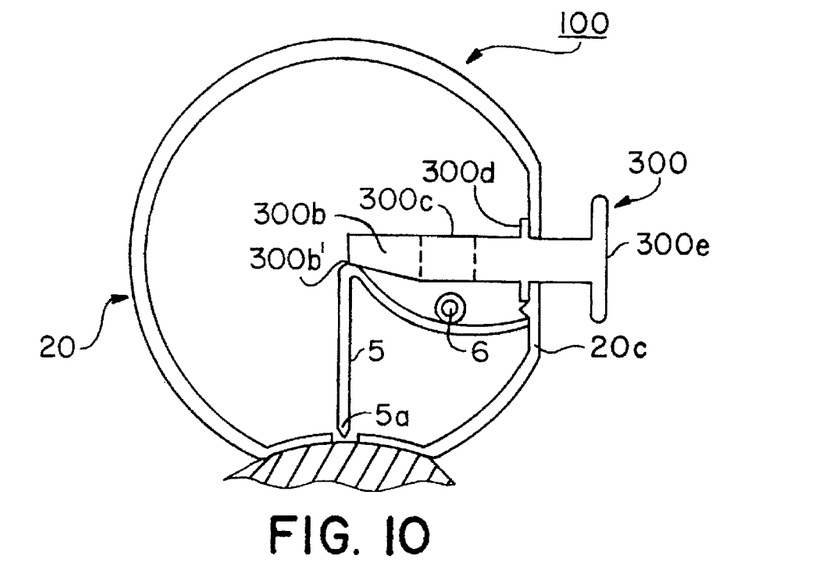
FIG. 10 is a sectional view of a third embodiment, with one face of the housing removed, showing the actuator in an initial position.

Similar to the first embodiment, when this embodiment is in the initial position, as shown in FIG. 10, the button 300e and an end of the shaft 300a extend from the peripheral surface 20c. This extension of the button 300e from the peripheral surface 20c is distinctly visible to even a casual observer. Thus, an operator can readily visibly identify a lancet device which has not been used.

As the actuator passes the actuating position (actuating position shown in FIG. 11) and the lancing function is completed, the spring is then returned to the locked position, as described above and as shown in FIG. 12. In this position, the button 300e contacts the outer surface of the peripheral surface 20c. This contact of the button 300e with the peripheral surface 20c is distinctly visible to even a casual observer. Thus, an operator can readily visibly identify a lancet device which has been used and needs to be discarded. This readily identifiable feature of the device prevents even a second contact of the device with the skin of a second patient, while also positively preventing a re-use of the device.

Figure 11:
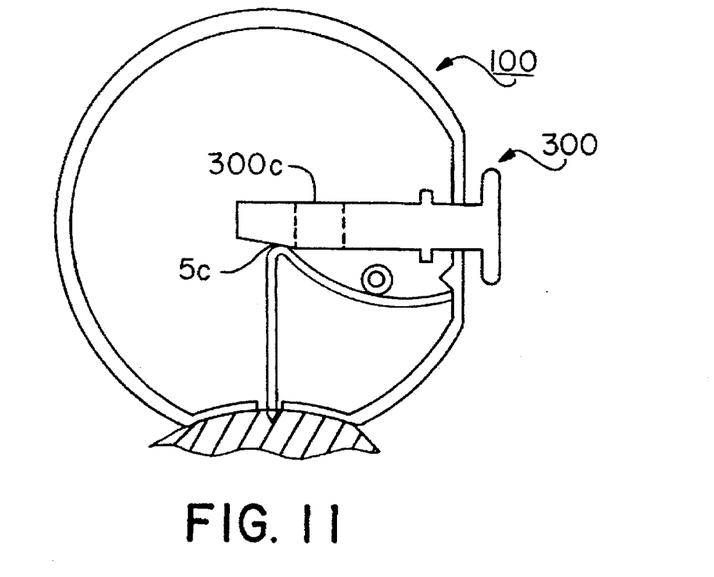
FIG. 11 is a sectional view of the third embodiment, with one face of the housing removed, showing the actuator in a biasing position.
Figure 13:
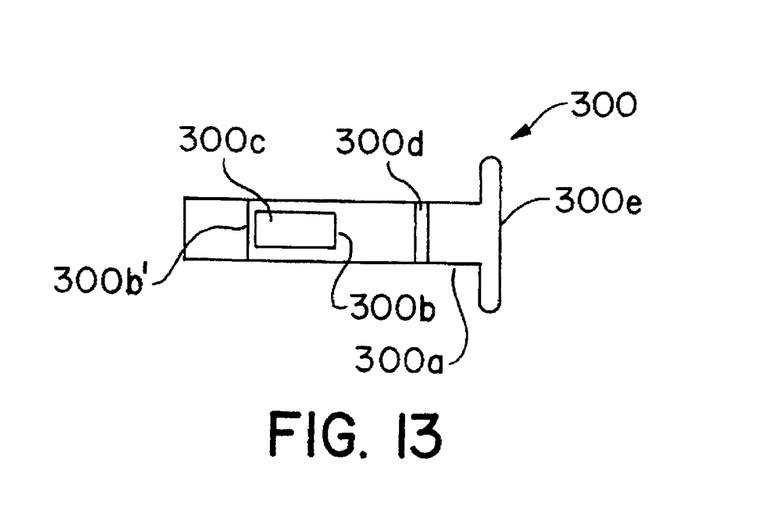
FIG. 13 is a side view of the actuator of the third embodiment showing the keyway thereof.

FIG. 13 shown as side view of the actuator 300 (i.e., in a plane perpendicular to the plane along which the actuator 300 is shown in FIG. 12), to more clearly show the configuration of the keyway 300c (keyway 300c being shown in phantom in FIGS. 10–12). Keyway 300c is essentially a notch which is cut or otherwise formed into shaft 300a, and which extends entirely therethrough, so as to form a hole through the entire thickness of the shaft 300a. Keyway 300c is shaped and dimensioned to readily accept the spring mechanism 5 within and to act as a locking device against which the spring mechanism abuts, should an attempt be made to return the actuator to the initial position.

Although the invention has been described with reference to particular means, materials and embodiments, it is to be understood that the invention is not limited to the particulars disclosed and extends to all equivalents within the scope of the claims.

What is claimed is:

1. A single use disposable lancet device comprising:
    a housing;
    a spring mechanism pivotally mounted in said housing, said spring mechanism comprising a sharpened end, wherein said spring mechanism is mounted within said housing in a substantially unbiased state; and
    an actuator for biasing said spring mechanism, said actuator being movable, with respect to said housing, from an initial position to a biasing position to a locked position, in that order;
    said actuator including a locking device which engages said spring mechanism for preventing movement of said actuator from said locked position;
    said housing including an opening sized to permit said sharpened end to protrude therethrough exteriorly of said housing upon biasing of said spring mechanism, and said sharpened end retracting back inside of said housing in said locked position; and
    said spring mechanism and said sharpened end being mounted within said housing in a substantially unbiased state when said actuator is in said initial position, said spring mechanism being biased by said actuator when said actuator is in said biased position causing said sharpened end to protrude from said housing, and said spring mechanism returning to a substantially unbiased state when said actuator is in said locked position.

2. A single use disposable lancet device as recited in claim 1, further comprising:
    a pivot post mounted within said housing;
    wherein said spring mechanism is pivotally mounted around said pivot post and is pivotally biased with respect to said pivot post upon biasing by said actuator.

3. A single use disposable lancet device as recited in claim 1, further comprising:
    a stop mounted within said housing;
    wherein said spring mechanism comprises a second end opposite said sharpened end, said second end being stopped from movement in a predetermined direction by said stop during biasing of said spring mechanism.

4. A single use disposable lancet device as recited in claim 1, wherein said housing comprises two face components joined by a peripheral surface to form a compartment within.

5. A single use disposable lancet device as recited in claim 4, wherein said actuator is mounted substantially centrally of one of said face components.

6. A single use disposable lancet device as recited in claim 4, wherein said actuator is mounted through said peripheral surface.

7. A single use disposable lancet device as recited in claim 4, wherein said housing is substantially disk-shaped with said two face components comprising two substantially circular faces and said peripheral surface joining said circular faces along circumferential edges.

8. A single use disposable lancet device as recited in claim 1, wherein said actuator comprises:

a button actuatable by one or more fingers of a user;

a shaft extending from said button and extending into said housing; and a biasing portion for contacting and biasing said spring mechanism upon movement of said actuator from said initial position to said biasing position;

wherein said button visibly extends from said housing in said initial position.

9. A single use disposable lancet device as recited in claim 8, wherein said biasing portion comprises a ramped fin extending from said shaft for progressive biasing of said spring mechanism as said button is pushed nearer said housing.

10. A single use disposable lancet device as recited in claim 9, wherein said locking device comprises a notch formed between an end of said ramped fin, said shaft, and said button, wherein, upon fully depressing said button so as to abut said housing, said spring mechanism slides off said ramped fin and into said notch, thereby returning to a substantially unbiased condition and preventing return of said actuator to said initial position;

wherein, when in said initial position, said button extends from said housing so that a user can readily visually identify said initial position and know that the lancet device has yet to be used; and wherein, when in said locked position, said button is approximate said housing so that a user can readily visually identify said locked position and know that the lancet device has been used and is to be disposed of.

11. A single use disposable lancet device as recited in claim 8, wherein said actuator further comprises:

a flange extending from an end of said shaft opposite an end of said shaft which extends from said button;

wherein said flange abuts said spring mechanism in said initial position and prevents removal of said actuator from said housing.

12. A single use disposable lancet device as recited in claim 8, wherein said biasing portion comprises a taper on an end of said shaft opposite an end of said shaft extending from said button, and an untapered portion of said shaft extending from said taper for progressive biasing of said spring mechanism as said button is pushed nearer said housing.

13. A single use disposable lancet device as recited in claim 12, wherein said locking device comprises a notch formed in said shaft, between said untapered portion and said end of said shaft extending from said button, wherein, upon fully depressing said button so as to abut said housing, said spring mechanism slides off said untapered portion and into said notch, thereby returning to a substantially unbiased condition and preventing return of said actuator to said initial position;

wherein, when in said initial position, a user can readily visually identify said initial position and know that the lancet device has yet to be used; and wherein, when in said locked position, a user can readily visually identify said locked position and know that the lancet device has been used and is to be disposed of.

14. A single use disposable lancet device as recited in claim 13, wherein said actuator further comprises:

a flange extending from said shaft between said notch and said end of said shaft which extends from said button;

wherein said flange abuts an internal surface of said housing when said actuator is in said initial position and prevents removal of said actuator from said housing.

15. A single use disposable lancet device as recited in claim 12, wherein said locking device comprises a keyway formed through said shaft, between said untapered portion and said end of said shaft extending from said button, wherein, upon fully depressing said button so as to abut said housing, said spring mechanism slides off said untapered portion and into said keyway, thereby returning to a substantially unbiased condition and preventing return of said actuator to said initial position;

wherein, when in said initial position, a user can readily visually identify said initial position and know that the lancet device has yet to be used; and wherein, when in said locked position, a user can readily visually identify said locked position and know that the lancet device has been used and is to be disposed of.

16. A single use disposable lancet device as recited in claim 15, wherein said actuator further comprises:

a flange extending from said shaft between said keyway and said end of said shaft which extends from said button;

wherein said flange abuts an internal surface of said housing when said actuator is in said initial position and prevents removal of said actuator from said housing.

17. A single use disposable lancet device comprising:

a housing;

a spring mechanism mounted to said housing, said spring mechanism comprising a sharpened end, wherein said spring mechanism is mounted within said housing in a substantially unbiased state;

an actuator for biasing said spring mechanism, wherein said actuator is movable, with respect to said housing, to bias said spring mechanism to extend said sharpened end so as to protrude from said housing;

means for indicating that the lancet device has not been used and that the lancet device has been used, wherein said means for indicating is movable with said actuator to move from indicating that the lancet device has not been used and that the lancet device has been used; and means for preventing re-use of the lancet device after a single use has been accomplished, wherein said means for preventing engages said actuator upon protrusion of said sharpened end from said housing.

18. A single use disposable lancet device as recited in claim 17, wherein said actuator comprises:

a button actuatable by one or more fingers of a user;

a shaft extending from said button and extending into said housing; and a biasing portion for contacting and biasing said spring mechanism upon movement of button toward said housing;

wherein said means for indicating that the lancet device has not been used and has been used comprises two positions of said button with respect to said housing wherein said button visibly extends from said housing to show that the lancet device has not been used, and wherein said button visibly contacts said housing to show that the lancet device has been used; and wherein said means for preventing re-use of the lancet device after a single use has been accomplished comprises a locking mechanism which locks said button in the position wherein said button contacts said housing, thereby preventing retraction of said button and preventing said actuator from biasing said spring mechanism more than one time.

19. A single use disposable lancet device as recited in claim 17, wherein said actuator comprises:

a button actuatable by one or more fingers of a user;

a shaft extending from said button and extending into said housing; and a biasing portion for contacting and biasing said spring mechanism upon movement of button toward said housing;

wherein said means for indicating that the lancet device has not been used and has been used comprises two positions of said button with respect to said housing wherein said button visibly extends from said housing to show that the lancet device has not been used, and wherein said button is substantially flush with said housing to show that the lancet device has been used; and wherein said means for preventing re-use of the lancet device after a single use has been accomplished comprises a locking mechanism which locks said button in the position wherein said button contacts said housing, thereby preventing retraction of said button and preventing said actuator from biasing said spring mechanism more than one time.

20. A single use disposable lancet device as recited in claim 18, wherein said button includes an element to prevent actuation of the button.

21. A single use disposable lancet device as recited in claim 19, wherein said button includes an element to prevent actuation of the button.

* * * * *